(12) United States Patent
Ralko

(10) Patent No.: US 6,758,453 B1
(45) Date of Patent: Jul. 6, 2004

(54) BOTTLE SUSPENSION DEVICE

(76) Inventor: George Ralko, 1723 Loney St. 1st Flr, Philadelphia, PA (US) 19111

( * ) Notice: Subject to any disclaimer, the term of this patent is extended or adjusted under 35 U.S.C. 154(b) by 0 days.

(21) Appl. No.: 10/388,928

(22) Filed: Mar. 14, 2003

(51) Int. Cl.⁷ .................................................. A47K 1/08
(52) U.S. Cl. .................................... 248/311.3; 248/104
(58) Field of Search .............................. 248/312, 312.1, 248/311.3, 102, 103, 104, 105, 107, 318; 215/399, DIG. 3

(56) References Cited

U.S. PATENT DOCUMENTS

| 1,559,740 | A | * | 11/1925 | Cardarella |
| 2,060,194 | A | * | 11/1936 | Gissubel |
| 2,084,243 | A | * | 6/1937 | Charles |
| 2,539,698 | A | * | 1/1951 | Pearson |
| 3,144,230 | A | * | 8/1964 | Brooks |
| 3,366,360 | A | * | 1/1968 | Burke |
| 3,395,882 | A | * | 8/1968 | Marshall |
| 3,630,477 | A | * | 12/1971 | Stadler ........................ 248/318 |
| 3,966,160 | A | * | 6/1976 | Wilson ..................... 248/311.3 |
| 4,776,546 | A | * | 10/1988 | Goldson et al. ............ 248/102 |
| 4,969,580 | A |   | 11/1990 | Makhail |
| 5,135,125 | A |   | 8/1992 | Andel et al. |
| 5,873,551 | A | * | 2/1999 | Jones ......................... 248/102 |

FOREIGN PATENT DOCUMENTS

DE          25 14 333 A1 *   2/1975

* cited by examiner

Primary Examiner—Gwendolyn Baxter

(57) ABSTRACT

A bottle suspension device for suspending a bottle upside down to facilitate dispensing of all of the contents of the bottle. The bottle suspension device includes a belt member comprising a first loop portion and a second loop portion. The first loop portion is designed for being positioned around a neck of the bottle. The second loop portion is designed for extending around a body of the bottle. The belt member is designed for selectively engaging a support structure to suspend the bottle from the support structure.

6 Claims, 3 Drawing Sheets

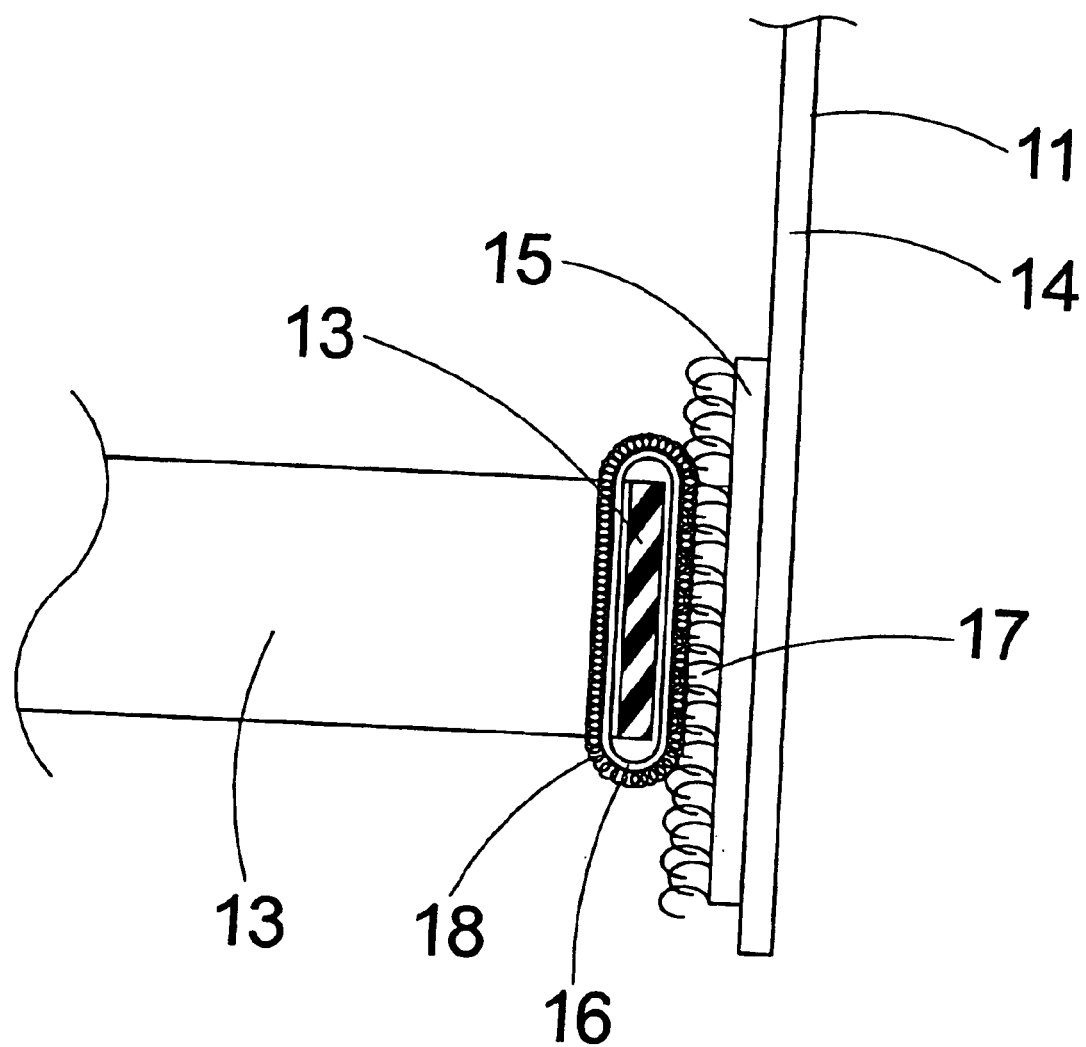

BOTTLE SUSPENSION DEVICE

BACKGROUND OF THE INVENTION

1. Field of the Invention

The present invention relates to bottle hangers and more particularly pertains to a new bottle suspension device for suspending a bottle upside down to facilitate dispensing of all of the contents of the bottle.

2. Description of the Prior Art

The use of bottle hangers is known in the prior art. U.S. Pat. No. 4,969,580 describes a device for supporting a bottle in an inverted state from a pipe in a shower stall. Another type of bottle hanger is U.S. Pat. No. 3,366,360 having a harness for being positioned around a bottle so that the bottle is supported in an inverted state. U.S. Pat. No. 5,135,125 has a label that is coupled to an intravenous bottle to identify the contents and allows the bottle to hung in an inverted state.

While these devices fulfill their respective, particular objectives and requirements, the need remains for a device that has certain improved features allowing for the angle of the strap to be changed to accommodate different types of support structures.

SUMMARY OF THE INVENTION

The present invention meets the needs presented above by providing the second fastener member being formed into loop so that the second loop portion extends through the loop and allows the second fastener member to be slid around the second loop portion and change the angle of the strap portion.

Still yet another object of the present invention is to provide a new bottle suspension device that is comprised of elastic material to accommodate bottles of varying sizes.

Even still another object of the present invention is to provide a new bottle suspension device that can be used in the kitchen for food dispensing items, while exercising to support a water bottle and in the shower for body cleansing products.

To this end, the present invention generally comprises a belt member comprising a first loop portion and a second loop portion. The first loop portion is designed for being positioned around a neck of the bottle. The second loop portion is designed for extending around a body of the bottle. The belt member is designed for selectively engaging a support structure to suspend the bottle from the support structure.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view of the present invention taken along line 3—3 of FIG. 1.

DESCRIPTION OF THE PREFERRED EMBODIMENT

Figure 1:
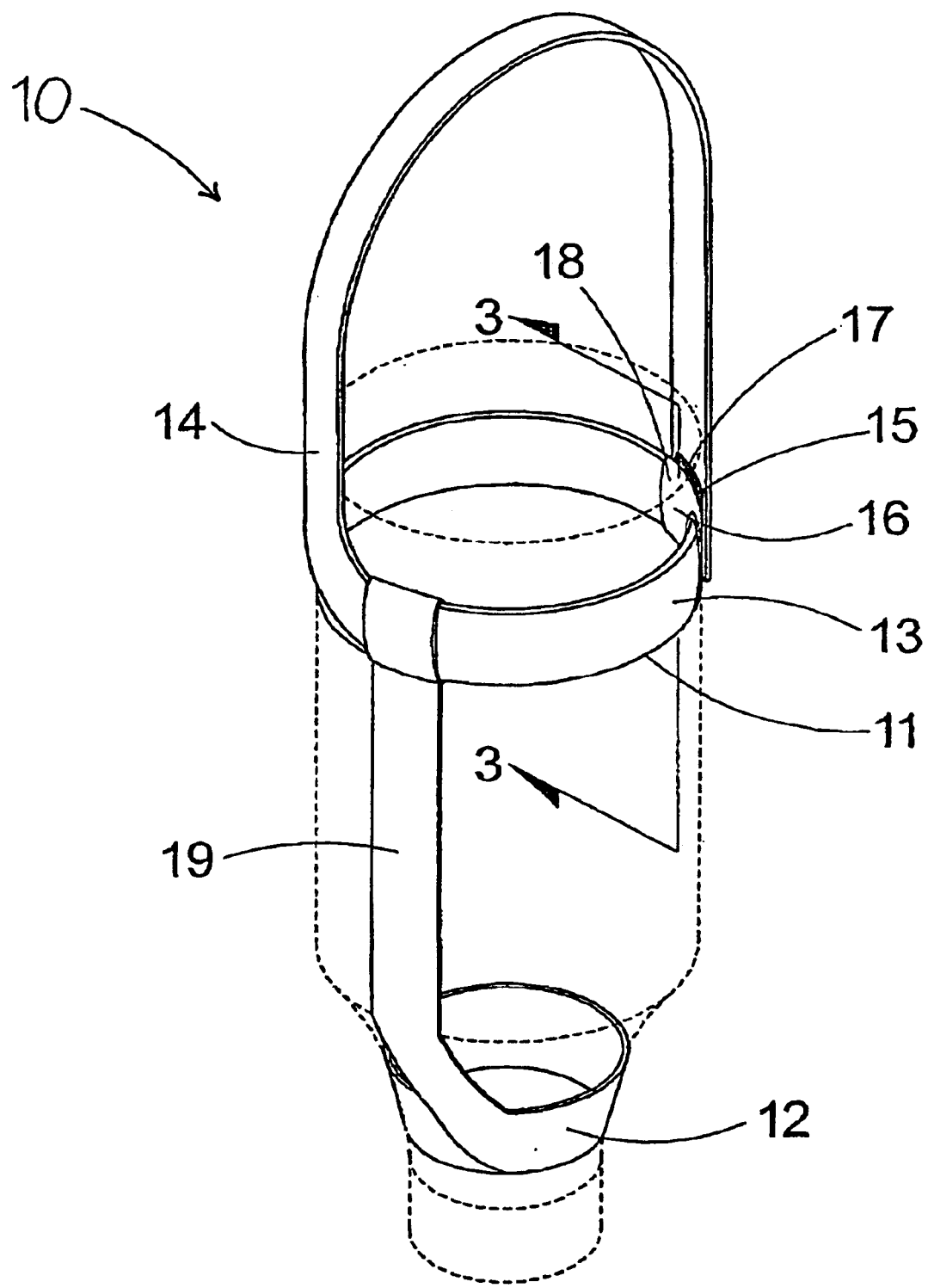
FIG. 1 is a perspective view of a new bottle suspension device according to the present invention shown in use.
Figure 2:
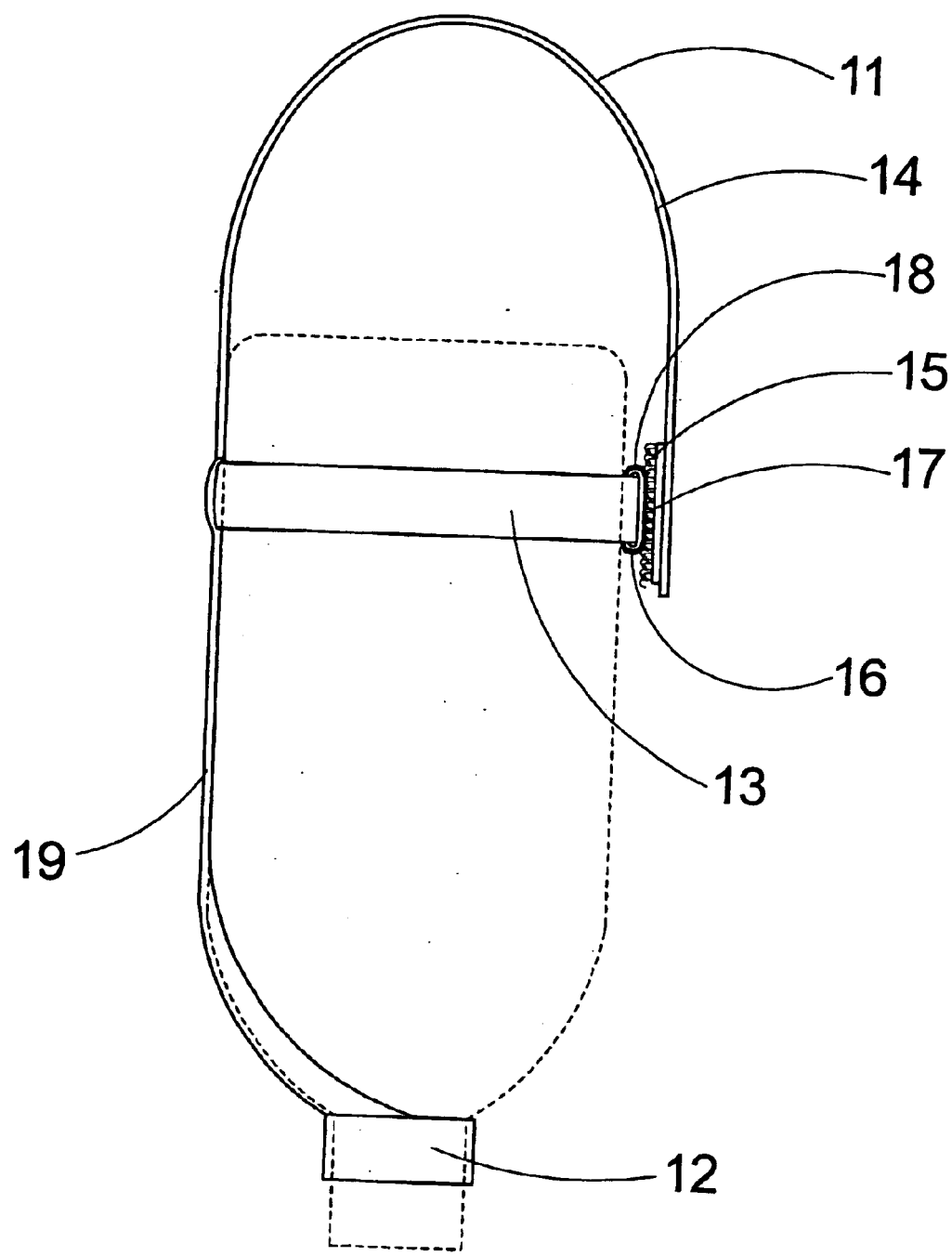
FIG. 2 is a front view of the present invention shown in use.

With reference now to the drawings, and in particular to FIGS. 1 through 3 thereof, a new bottle suspension device embodying the principles and concepts of the present invention and generally designated by the reference numeral 10 will be described.

As best illustrated in FIGS. 1 through 3, the bottle suspension device 10 generally comprises a belt member 11 comprising a first loop portion 12 and a second loop portion 13. The first loop portion 12 is designed for being positioned around a neck of the bottle. The second loop portion 13 is designed for extending around a body of the bottle. The belt member 11 is designed for selectively engaging a support structure to suspend the bottle from the support structure. The first loop portion 12 comprises a diameter less than a diameter of the second loop portion 13. The first loop portion 12 is designed for inhibiting the bottle from slipping out of the second loop portion 13 when the belt member 11 suspends the bottle from the support structure. The support structure may comprise a shower bar, a towel bar or a hook with a suction cup attached for use on smooth surfaces.

The belt member 11 comprises a strap portion 14. The strap portion 14 is coupled to the second loop portion 13 of the belt member 11. The strap portion 14 is designed for extending around the support structure whereby the strap portion 14 of the belt member 11 suspends the bottle from the support structure upside down to allow contents of the bottle to flow towards the neck of the bottle.

A first fastener member 15 is coupled to a free end of the strap portion 14. A second fastener member 16 is coupled to the second loop portion 13. The first fastener member 15 is complimentary to the second fastener member 16 for securing the free end of the strap portion 14 to the second loop portion 13 of the belt member 11 whereby the first fastener member 15 and the second fastener member 16 are designed for permitting the strap portion 14 to be extended around the support structure and secured to the second loop portion 13 to secure the bottle to the support structure.

The first fastener member 15 comprises a first portion of hook and loop fastener 17. The second fastener member 16 comprises a second portion of hook and loop fastener 18. The first portion of hook and loop fastener 17 is complimentary to the second portion of hook and loop fastener 18 for permitting the free end of the strap portion 14 to be selectively coupled to the second loop portion 13.

The second fastener member 16 is formed in a loop. The second loop portion 13 extends through the loop formed by the second fastener portion. The second fastener member 16 is slidably coupled to the second loop portion 13 whereby the second fastener member 16 is selectively positionable along the second loop portion 13 to allow the strap portion 14 to be positioned at a variety of angles with respect to the second loop portion 13.

The belt member 11 comprises a suspension portion 19. The suspension portion 19 extends between the second loop portion 13 and the first loop portion 12. The suspension portion 19 is for maintaining a distance between the first loop portion 12 and the second portion when the belt member 11 is coupled to the bottle. The suspension portion 19 has a length between about 2 inches to about 3 inches.

The belt member 11 comprises an elastic material. The elastic material is designed for permitting the belt member 11 to engage variety of different sized bottles. The elastic material has a width between about ¾ on an inch to about 1 inch.

In use, the user slides the neck of bottle through the second loop portion 13 and into the first loop portion 12. The user then makes sure the second loop portion 13 is secure around the body of the bottle. The strap portion 14 is then extended around the support structure and the first fastener member 15 is secured to the second fastener member 16. The second fastener member 16 is then slid around the second loop portion 13 to provide an angle of the strap portion 14 that is the most secure for supporting the bottle. The user is then free to open the bottle and dispense the contents of the bottle as needed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bottle suspension device for suspending bottles upside down from a support, the bottle suspension device comprising:
    a belt member comprising a first loop portion and a second loop portion, said first loop portion being adapted for being positioned around a neck of the bottle, said second loop portion being adapted for extending around a body of the bottle, said belt member being adapted for selectively engaging a support structure to suspend the bottle from the support structure;
    said belt member comprising a strap portion, said strap portion being coupled to said second loop portion of said belt member, said strap portion being adapted for extending around the support structure such that said strap portion of said belt member suspends the bottle from the support structure upside down to allow contents of the bottle to flow towards the neck of the bottle;
    a first fastener member being coupled to a free end of said strap portion, a second fastener member being coupled to said second loop portion, said first fastener member being complimentary to said second fastener member for securing said free end of said strap portion to said second loop portion of said belt member such that said first fastener member and said second fastener member are adapted for permitting said strap portion to be extended around the support structure and secured to said second loop portion to secure the bottle to the support structure; and
    said second fastener member being formed in a loop, said second loop portion extending through said loop formed by said second fastener portion, said second fastener member being slidably coupled to said second loop portion such that said second fastener member is selectively positionable along said second loop portion to allow said strap portion to be positioned at a variety of angles with respect to said second loop portion.

2. The bottle suspension device as set forth in claim 1, further comprising:
    said first fastener member comprising a first portion of hook and loop fastener, said second fastener member comprising a second portion of hook and loop fastener, said first portion of hook and loop fastener being complimentary to said second portion of hook and loop fastener for permitting said free end of said strap portion to be selectively coupled to said second loop portion.

3. The bottle suspension device as set forth in claim 1, further comprising:
    said belt member comprising a suspension portion, said suspension portion extending between said second loop portion and said first loop portion, said suspension portion being for maintaining a distance between said first loop portion and said second portion when said belt member is coupled to the bottle.

4. The bottle suspension device as set forth in claim 1, further comprising:
    said first loop portion comprising a diameter less than a diameter of said second loop portion, said first loop portion being adapted for inhibiting the bottle from slipping out of said second loop portion when said belt member suspends the bottle from the support structure.

5. The bottle suspension device as set forth in claim 1, further comprising:
    said belt member comprising an elastic material, said elastic material being adapted for permitting said belt member to engage variety of different sized bottles.

6. A bottle suspension device for suspending bottles upside down from a support, the bottle suspension device comprising:
    a belt member comprising a first loop portion and a second loop portion, said first loop portion being adapted for being positioned around a neck of the bottle, said second loop portion being adapted for extending around a body of a bottle, said belt member being adapted for selectively engaging a support structure to suspend the bottle from the support structure;
    said belt member comprising a strap portion, said strap portion being coupled to said second loop portion of said belt member, said strap portion being adapted for extending around the support structure such that said strap portion of said belt member suspends the bottle from the support structure upside down to allow contents of the bottle to flow towards the neck of the bottle;
    a first fastener member being coupled to a free end of said strap portion, a second fastener member being coupled to said second loop portion, said first fastener member being complimentary to said second fastener member for securing said free end of said strap portion to said second loop portion of said belt member such that said first fastener member and said second fastener member are adapted for permitting said strap portion to be extended around the support structure and secured to said second loop portion to secure the bottle to the support structure;
    said first fastener member comprising a first portion of hook and loop fastener, said second fastener member comprising a second portion of hook and loop fastener, said first portion of hook and loop fastener being complimentary to said second portion of hook and loop fastener for permitting said free end of said strap portion to be selectively coupled to said second loop portion;

said second fastener member being formed in a loop, said second loop portion extending through said loop formed by said second fastener portion, said second fastener member being slidably coupled to said second loop portion such that said second fastener member is selectively positionable along said second loop portion to allow said strap portion to be positioned at a variety of angles with respect to said second loop portion;

said belt member comprising a suspension portion, said suspension portion extending between said second loop portion and said first loop portion, said suspension portion being for maintaining a distance between said first loop portion and said second portion when said belt member is coupled to the bottle;

said first loop portion comprising a diameter less than a diameter of said second loop portion, said first loop portion being adapted for inhibiting the bottle from slipping out of said second loop portion when said belt member suspends the bottle from the support structure; and said belt member comprising an elastic material, said elastic material being adapted for permitting said belt member to engage variety of different sized bottles.

* * * * *